United States Patent
Mitamura et al.

(10) Patent No.: US 11,951,193 B2
(45) Date of Patent: Apr. 9, 2024

(54) MONOMER COMPOSITION FOR DENTAL MATERIALS, COMPOSITION FOR DENTAL MATERIALS, AND DENTAL MATERIAL

(71) Applicant: MITSUI CHEMICALS, INC., Tokyo (JP)

(72) Inventors: Takenori Mitamura, Chiba (JP); Yoko Kosugi, Ichihara (JP)

(73) Assignee: MITSUI CHEMICALS, INC., Tokyo (JP)

( * ) Notice: Subject to any disclaimer, the term of this patent is extended or adjusted under 35 U.S.C. 154(b) by 472 days.

(21) Appl. No.: 17/286,838

(22) PCT Filed: Dec. 24, 2019

(86) PCT No.: PCT/JP2019/050586
§ 371 (c)(1),
(2) Date: Apr. 20, 2021

(87) PCT Pub. No.: WO2020/138071
PCT Pub. Date: Jul. 2, 2020

(65) Prior Publication Data
US 2021/0338537 A1  Nov. 4, 2021

(30) Foreign Application Priority Data
Dec. 28, 2018 (JP) .................... 2018-247972

(51) Int. Cl.
*A61K 6/887* (2020.01)
*A61K 6/30* (2020.01)
*C08L 33/10* (2006.01)

(52) U.S. Cl.
CPC ............ *A61K 6/887* (2020.01); *A61K 6/30* (2020.01); *C08L 33/10* (2013.01)

(58) Field of Classification Search
CPC combination set(s) only.
See application file for complete search history.

(56) References Cited

U.S. PATENT DOCUMENTS

| 2013/0047887 | A1* | 2/2013 | Trujillo-Lemon | A61K 6/78 106/35 |
| 2014/0131908 | A1* | 5/2014 | Sun | B33Y 80/00 264/16 |
| 2017/0165152 | A1* | 6/2017 | Eckert | A61K 6/887 |
| 2019/0374440 | A1* | 12/2019 | Kosugi | C09J 4/00 |

FOREIGN PATENT DOCUMENTS

| JP | 2017506245 A | 3/2017 |
| JP | 2018145133 A | 9/2018 |
| WO | 2011041677 A2 | 4/2011 |
| WO | 2018181707 A1 | 10/2018 |
| WO | WO-2018181707 A1 * | 10/2018 ............ A61K 6/30 |

* cited by examiner

*Primary Examiner* — Peter A Salamon
(74) *Attorney, Agent, or Firm* — BUCHANAN, INGERSOLL & ROONEY PC

(57) ABSTRACT

A monomer composition for a dental material including a compound represented by Formula (1). In Formula (1), X represents an n-valent organic group having from 1 to 200 carbon atoms and containing at least one selected from the group consisting of an oxygen atom and a nitrogen atom, in which the at least one selected from the group consisting of an oxygen atom and a nitrogen atom is bound to Y; and each Y represents a (meth)acryloyl group-containing group (Y1) represented by the following Formula (A), a (meth)acryloyl group (Y2), a hydrogen atom, or a hydrocarbon group having from 1 to 20 carbon atoms, with the proviso that at least one or more Y, among all Ys included in the compound represented by Formula (1), is the (meth)acryloyl group-containing group (Y1).

15 Claims, No Drawings

MONOMER COMPOSITION FOR DENTAL MATERIALS, COMPOSITION FOR DENTAL MATERIALS, AND DENTAL MATERIAL

TECHNICAL FIELD

The present disclosure relates to a monomer composition for a dental material, a composition for a dental material, and a dental material.

BACKGROUND ART

In clinical settings for dental treatment, resin-based materials for use in tooth repair are increasingly used in a wider range of applications. Resin-based dental materials may sometimes contain monomers containing (meth)acrylate groups in the molecular structures thereof. Examples of the above described monomers typically include dimethacrylates having (meth)acrylic groups on both ends thereof, such as bisphenol A diglycidyl methacrylate (Bis-GMA) and 2,2,4-trimethylhexamethylene bis(2-carbamoyloxyethyl) dimethacrylate (UDMA).

For example, Japanese Patent Application Laid-Open (JP-A) No. 2018-145133 describes 10-methacryloyloxydecyl dihydrogen phosphate (MDP), triethylene glycol dimethacrylate (TEGDMA), 2-hydroxyethyl methacrylate (HEMA) and the like, as the monomers described above.

These monomers are properly selected and used depending on the characteristics (for example, mechanical properties such as adhesion and strength, and handleability) which are required for dental materials obtained using compositions into which these monomers are incorporated.

SUMMARY OF INVENTION

Technical Problem

However, it cannot be said that a combination of the above described monomers alone is sufficient in terms of the strength and adhesion to be imparted to the dental materials, and there was room for improvement.

The present disclosure aims to address the above mentioned problems.

In other words, one embodiment of the present disclosure relates to providing: a monomer composition for a dental material which imparts an excellent flexural strength to the resulting cured product in an application as a dental filler, such as a composite resin or a resin cement, and provides an improved adhesion in an application as a dental adhesive, such as a bonding material; a composition for a dental material including the same; and a dental material which is a cured product thereof.

Solution to Problem

The present disclosure include the following aspects.
<1> A monomer composition for a dental material, comprising a compound represented by the following Formula (1):

$$X\!\!-\!\!(Y)_n \quad (1)$$

wherein, in Formula (1): X represents an n-valent organic group having from 1 to 200 carbon atoms and containing at least one selected from the group consisting of an oxygen atom and a nitrogen atom, wherein the at least one selected from the group consisting of an oxygen atom and a nitrogen atom is bound to Y;

each Y represents a (meth)acryloyl group-containing group (Y1) represented by the following Formula (A), a (meth)acryloyl group (Y2), a hydrogen atom, or a hydrocarbon group having from 1 to 20 carbon atoms, with the proviso that at least one or more Y, among all Ys included in the compound represented by Formula (1), is the (meth)acryloyl group-containing group (Y1);

a plurality of Ys may be the same as or different from each other; and n represents an integer of 3 or more

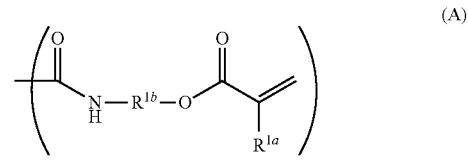

wherein, in Formula (A), $R^{1a}$ represents a hydrogen atom or a methyl group; and $R^{1b}$ represents a divalent organic group having from 2 to 6 carbon atoms, which may be substituted with an alkyl group having from 1 to 6 carbon atoms or a (meth)acryloyloxyalkylene group).

<2> The monomer composition for a dental material according to <1>, wherein the compound represented by Formula (1) has a molecular weight of from 350 to 2,000.

<3> The monomer composition for a dental material according to <1> or <2>, wherein at least two or more Ys, among all the Ys included in the compound represented by Formula (1), are the (meth)acryloyl group-containing group (Y1).

<4> The monomer composition for a dental material according to any one of <1> to <3>, wherein, in Formula (A), $R^{1b}$ is a linear alkylene group having from 2 to 6 carbon atoms or a linear oxyalkylene group having from 2 to 6 carbon atoms.

<5> The monomer composition for a dental material according to any one of <1> to <4>, wherein n is an integer from 3 to 12.

<6> The monomer composition for a dental material according to any one of <1> to <5>, wherein X is any one of groups represented by the following Formulae (X1) to (X10):

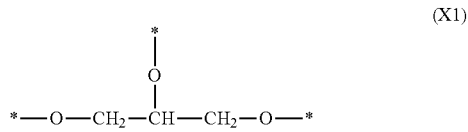

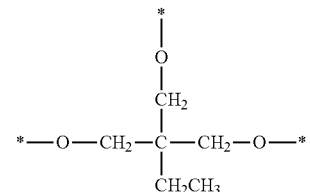

-continued

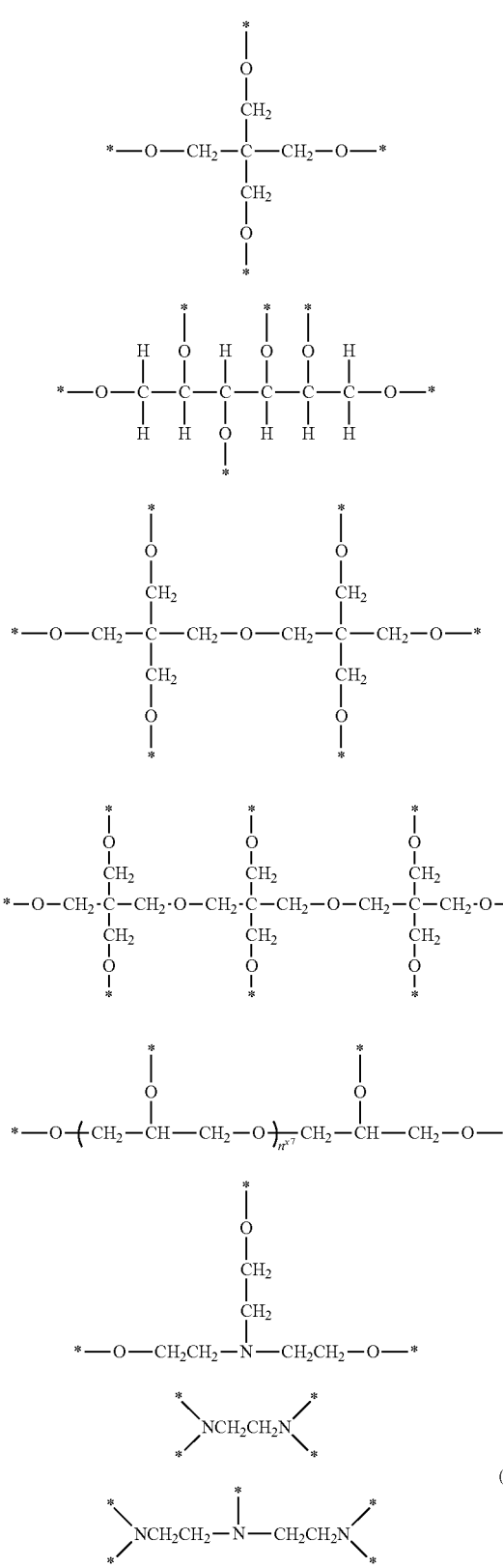

wherein, in Formulae (X1) to (X10), each * represents a bonding position; and wherein, in Formula (X7), $n^{x7}$ represents an integer from 1 to 40).

<7> The monomer composition for a dental material according to any one of claims <1> to <6>, wherein, in Formula (1), the at least one (meth)acryloyl group-containing group (Y1) comprises at least one selected from the group consisting of groups represented by the following Formulae (Y1a) to (Y1f):

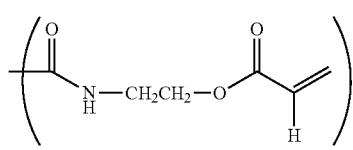
(Y1a)

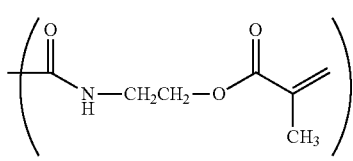
(Y1b)

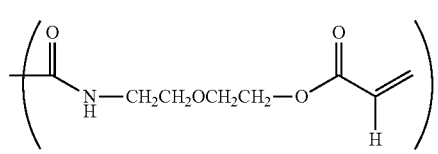
(Y1c)

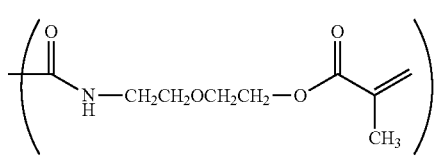
(Y1d)

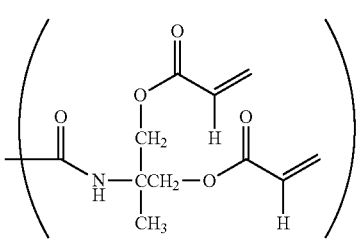
(Y1e)

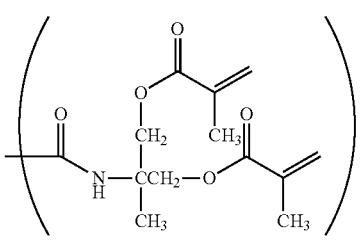
(Y1f)

<8> The monomer composition for a dental material according to any one of <1> to <7>, comprising, as the compound represented by Formula (1), at least one selected from the group consisting of the following compounds (1-1) to (1-10):

(1-1)
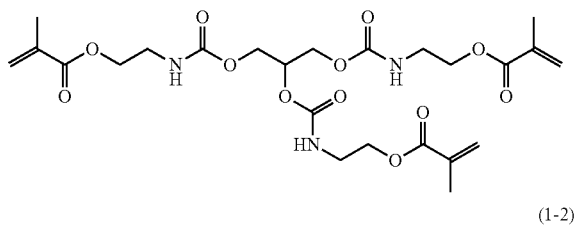

(1-2)
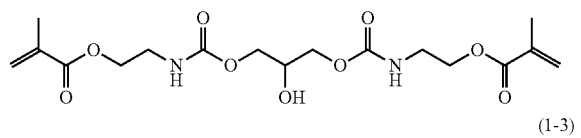

(1-3)
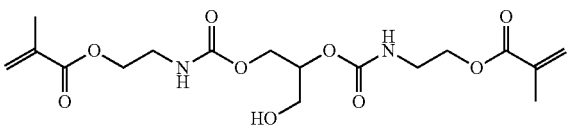

(1-4)
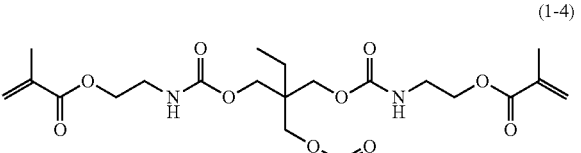

(1-5)
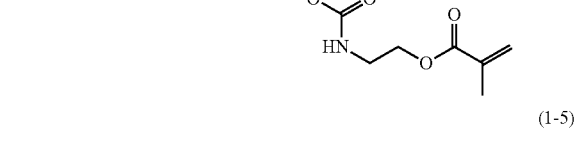

(1-6)
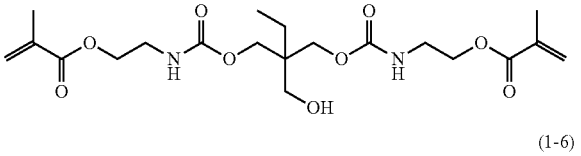

(1-7)
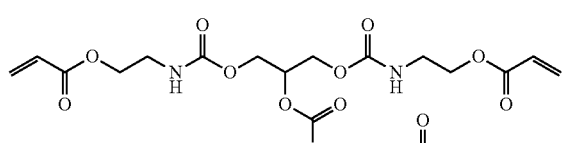

(1-8)
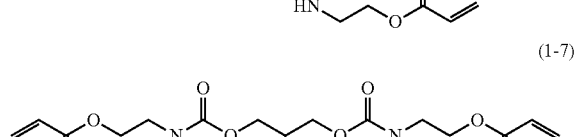

(1-9)
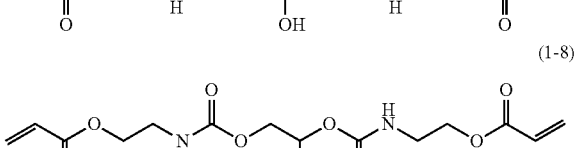

(1-10)
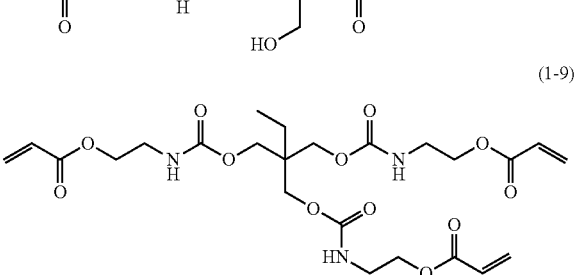

<9> The monomer composition for a dental material according to any one of <1> to <8>, further comprising a (meth)acrylate compound (2) other than the compound represented by Formula (1).

<10> The monomer composition for a dental material according to <9>, wherein a content of the compound represented by Formula (1) is from 1.0% by mass to 40.0% by mass, with respect to a total content of the compound represented by Formula (1) and the (meth)acrylate compound (2).

<11> The monomer composition for a dental material according to <9> or <10>, wherein the (meth)acrylate compound (2) is one or more compounds selected from the group consisting of an acidic group-containing (meth)acrylate, a monofunctional (meth)acrylate containing no acidic group, and a bifunctional (meth)acrylate containing no acidic group.

<12> The monomer composition for a dental material according to any one of <9> to <11>, wherein a total content of the compound represented by Formula (1) and the (meth)acrylate compound (2) is 90% by mass or more, with respect to a total amount of the monomer composition for a dental material.

<13> A composition for a dental material, comprising: the monomer composition for a dental material according to any one of <1> to <12>; and a polymerization initiator.

<14> The composition for a dental material according to <13>, wherein a content of the compound represented by Formula (1) is from 0.1% by mass to 20% by mass, with respect to a total mass of the composition for a dental material.

<15> The composition for a dental material according to <13> or <14>, wherein the composition is used as a dental adhesive resin cement, a dental composite resin, or a dental bonding material.

<16> A dental material which is a cured product of the composition for a dental material according to any one of <13> to <15>.

Advantageous Effects of Invention

One aspect of the present disclosure provides: a monomer composition for a dental material which imparts an excellent strength to the resulting cured product in an application as a dental filler, such as a composite resin or a resin cement, and provides an improved adhesion in an application as a dental adhesive, such as a bonding material; a composition for a dental material including the same; and a dental material which is a cured product thereof.

DESCRIPTION OF EMBODIMENTS

In the present disclosure, any numerical range indicated using an expression "from * to" represents a range in which numerical values described before and after the "to" are included in the range as a lower limit value and an upper limit value.

In the present disclosure, the amount of each component in a composition refers, in a case in which a plurality of substances corresponding to each component are present in the composition, to the total amount of the plurality of substances present in the composition, unless otherwise specified.

In a numerical range described in stages, in the present disclosure, the upper limit value or the lower limit value of one numerical range may be replaced with the upper limit value or the lower limit value of another numerical range described in stages. Further, in a numerical range described in stages, in the present disclosure, the upper limit value or the lower limit value of the numerical range may be replaced with a value shown in Examples.

In the present disclosure, the term "(meth)acryloyl" refers to acryloyl or methacryloyl, and the term "(meth)acrylate" refers to acrylate or methacrylate.

[Monomer Composition for Dental Material]

A monomer composition for a dental material according to the present disclosure includes a compound represented by the following Formula (1).

(1)

In Formula (1), X represents an n-valent organic group having from 1 to 200 carbon atoms and containing at least one selected from the group consisting of an oxygen atom and a nitrogen atom, wherein the at least one selected from the group consisting of an oxygen atom and a nitrogen atom is bound to Y.

Each Y represents a (meth)acryloyl group-containing group (Y1) represented by the following Formula (A), a (meth)acryloyl group (Y2), a hydrogen atom, or a hydrocarbon group having from 1 to 20 carbon atoms, with the proviso that at least one or more Y, among all Ys included in the compound represented by Formula (1), is the (meth)acryloyl group-containing groups (Y1); a plurality of Ys may be the same as or different from each other; and n represents an integer of 3 or more.

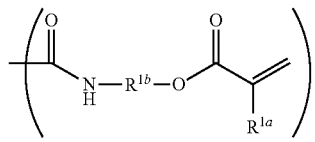

(A)

In Formula (A), $R^{1a}$ represents a hydrogen atom or a methyl group; and $R^{1b}$ represents a divalent organic group having from 2 to 6 carbon atoms, which may be substituted with an alkyl group having from 1 to 6 carbon atoms or a (meth)acryloyloxyalkylene group.

The use of the monomer composition for a dental material according to the present disclosure enables to impart an excellent flexural strength to the resulting cured product in an application as a dental filler, such as a composite resin or a resin cement, and to improve adhesion in an application as a dental adhesive, such as a bonding material.

In Formula (1), X is an n-valent organic group having from 1 to 200 carbon atoms and containing at least one selected from the group consisting of an oxygen atom and a nitrogen atom, and the n-valent organic group preferably has from 2 to 150 carbon atoms, and more preferably 3 to 30 carbon atoms.

The organic group containing at least one selected from the group consisting of an oxygen atom and a nitrogen atom preferably does not have a structure (for example, a structure represented by "—O—O—") in which oxygen atoms are successively present in a main chain, and the structures other than oxygen and nitrogen atoms are preferably hydrocarbon groups.

In Formula (1), n represents an integer of 3 or more, and is preferably an integer from 3 to 12, more preferably an integer from 3 to 6, and particularly preferably 3.

In Formula (1), X is preferably any one of the following Formulae (X1) to (X10), more preferably represented by any one of the following Formulae (X1) to (X7), still more preferably represented by any one of the following Formulae (X1) to (X5), and yet still more preferably represented by any one of the following Formulae (X1) to (X3).

However, $n^{X7}$ in the following Formula (X7) represents an integer from 1 to 40, and is preferably an integer from 1 to 20.

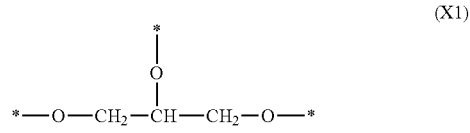

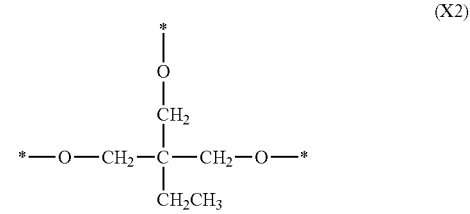

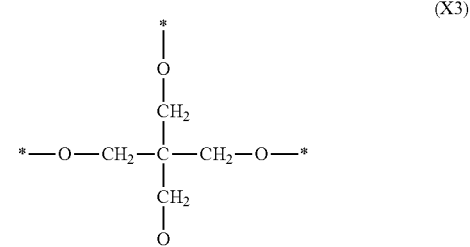

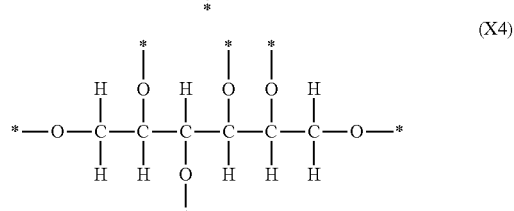

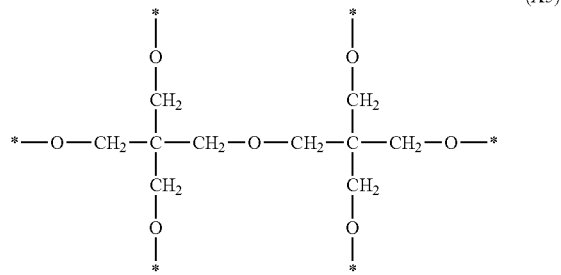

-continued

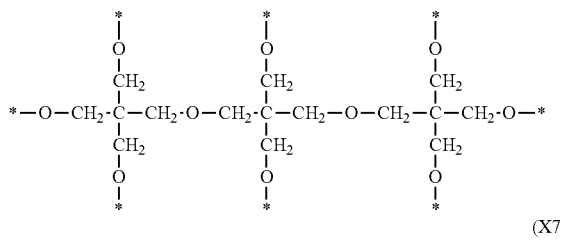
(X6)
(X7)

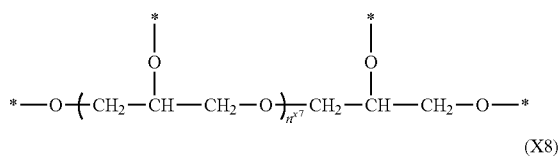
(X8)

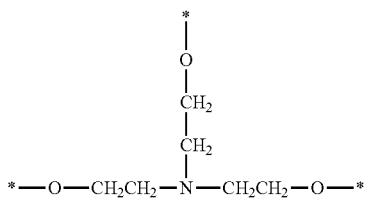
(X9)

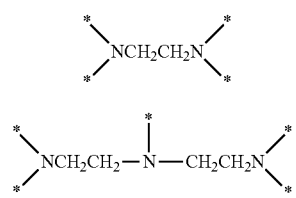
(X10)

In Formulae (X1) to (X10), each * represents a bonding position (bonding position to Y). In Formula (X7), $n^{X7}$ represents an integer from 1 to 40.

In Formula (1), each Y represents a (meth)acryloyl group-containing group (Y1) represented by the above described Formula (A), a (meth)acryloyl group (Y2), a hydrogen atom, or a hydrocarbon group having from 1 to 20 carbon atoms, and at least one Y, of all Ys included in the compound represented by Formula (1), is the (meth)acryloyl group-containing group (Y1).

It is preferred that at least two or more Ys are the (meth)acryloyl group-containing groups (Y1), it is more preferred that at least three or more Ys are the (meth)acryloyl group-containing groups (Y1), and it is still more preferred that all Ys are the (meth)acryloyl group-containing groups (Y1).

In a case in which Ys include a group other than the (meth)acryloyl group-containing groups (Y1), or a hydrogen atom, a hydrogen atom is preferably included. For example, it is preferred that one of all Ys is a hydrogen atom, and remaining Ys are the (meth)acryloyl group-containing groups (Y1).

In Formula (1), the hydrocarbon group having from 1 to 20 carbon atoms may be a linear hydrocarbon group, or may be a hydrocarbon group having a branched structure and/or a ring structure.

In Formula (1), n represents an integer of 3 or more, and is preferably an integer from 3 to 12, more preferably an integer from 3 to 6, and particularly preferably 3.

In Formula (A), $R^{1b}$ represents a divalent organic group having from 2 to 6 carbon atoms. $R^{1b}$ is preferably a linear alkylene group having from 2 to 6 carbon atoms or a linear oxyalkylene group having from 2 to 6 carbon atoms, more preferably a linear alkylene group having from 2 to 4 carbon atoms or a linear oxyalkylene group having from 2 to 4 carbon atoms, and still more preferably a linear alkylene group having from 2 to 4 carbon atoms. $R^{1b}$ may be substituted with an alkyl group having from 1 to 6 carbon atoms or a (meth)acryloyloxyalkylene group, or may be non-substituted.

The alkylene group in the (meth)acryloyloxyalkylene group may be, for example, an alkylene group having from 1 to 12 carbon atoms, and may specifically be a (meth)acryloyloxymethylene group, a (meth)acryloyloxyethylene group, a (meth)acryloyloxypropylene group or the like.

The (meth)acryloyl group-containing group (Y1) is preferably at least one selected from the group consisting of groups represented by the following Formulae (Y1a) to (Y1f), more preferably at least one selected from the group consisting of groups represented by the following Formulae (Y1a) to (Y1d), and still more preferably at least one selected from the group consisting of groups represented by the following Formulae (Y1a) and (Y1b):

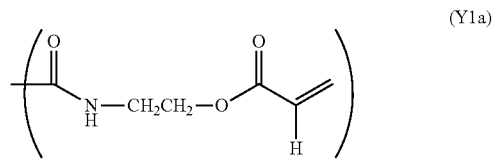
(Y1a)

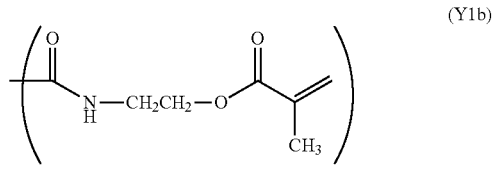
(Y1b)

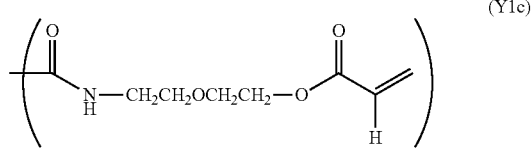
(Y1c)

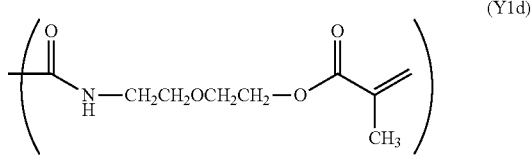
(Y1d)

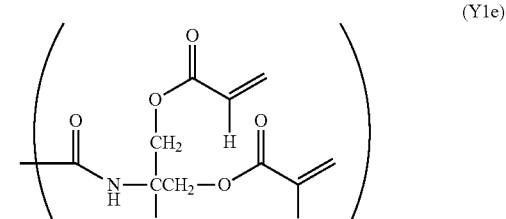
(Y1e)

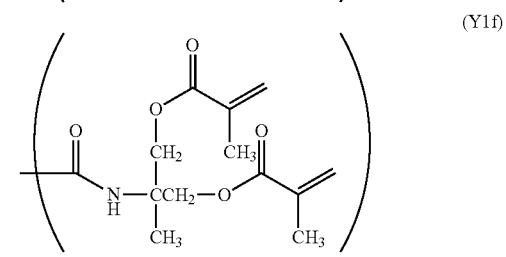
(Y1f)

The monomer composition preferably contains, as the compound represented by Formula (1), at least one selected from the group consisting of the following compounds (1-1) to (1-10), and more preferably contains the following compound (1-1), since the adhesion to enamel is improved, in particular.

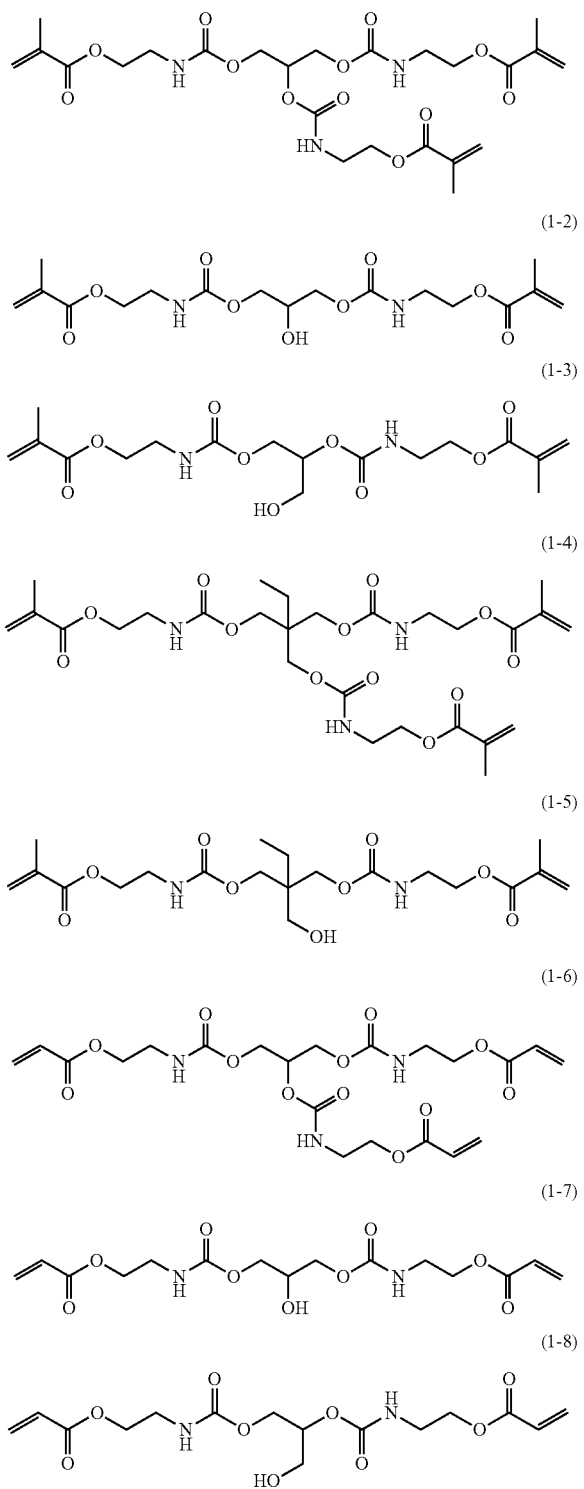

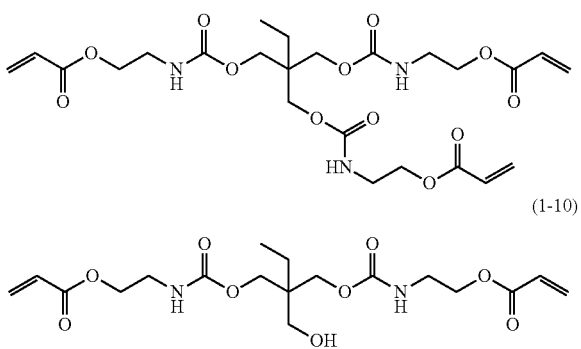

The compound represented by Formula (1) preferably has a molecular weight of from 350 to 2,000.

This enables to further improve the flexural strength of the resulting cured product.

From the above described point of view, the compound represented by Formula (1) more preferably has a molecular weight of from 380 to 1,500, and still more preferably from 400 to 700.

It is preferred that the monomer composition for a dental material according to the present disclosure further contains a (meth)acrylate compound (2) other than the compound represented by Formula (1).

The (meth)acrylate compound (2) is preferably one or more compounds selected from the group consisting of an acidic group-containing (meth)acrylate, a monofunctional (meth)acrylate containing no acidic group, and a bifunctional (meth)acrylate containing no acidic group.

Examples of the acidic group to be contained in the acidic group-containing (meth)acrylate include carboxylic acid group, carboxylic anhydride group, phosphate group, thiophosphate group, pyrophosphoric acid group, thiopyrophosphoric acid group, phosphonic acid group, thiophosphonic acid group and sulfonic acid group. These acidic groups may be in the form of acid chlorides, alkali metal salts, alkaline earth metal salts, ammonium salts and the like.

Examples of the acidic group-containing (meth)acrylate which contains a carboxylic acid group or a carboxylic anhydride group include 4-methacryloyloxyethyl trimellitic acid (4-MET) and anhydride thereof.

Examples of the acidic group-containing (meth)acrylate which contains a phosphate group include 10-methacryloyloxydecyl dihydrogen phosphate (MDP).

Examples of the monofunctional (meth)acrylate containing no acidic group include 2-hydroxyethyl acrylate (HEA), 2-hydroxyethyl methacrylate (HEMA), 2-hydroxypropyl acrylate (HPA), 2-hydroxypropyl methacrylate (HPMA), and 2-isocyanatoethyl methacrylate.

Examples of the bifunctional (meth)acrylate containing no acidic group include 2,2,4-trimethylhexamethylene bis (2-carbamoyloxyethyl) dimethacrylate (UDMA), neopentyl di(meth)acrylate, 1,4-butanediol di(meth)acrylate, 1,6-hexanediol di(meth)acrylate, 1,8-octanediol di(meth)acrylate, 1,9-nonanediol di(meth)acrylate, 1,10-decanediol di(meth)acrylate, tricyclodecanedimethanol di(meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, tetrapropylene glycol di(meth)acrylate, polypropylene glycol di(meth)acrylate, 2,2-bis[4-(3-(meth)acryloyloxy-2-hydroxypropoxy)phenyl]propane, ethylene oxide-modified bisphenol A di(meth)acrylate, and propylene oxide-modified bisphenol A di(meth)acrylate.

The total content of the compound represented by Formula (1) and the (meth)acrylate compound (2) is preferably 90% by mass or more, and more preferably 95% by mass or more, with respect to the total amount of the monomer composition for a dental material.

The content of the compound represented by Formula (1) is preferably from 1.0% by mass to 4.0% by mass, and more preferably from 3.0% by mass to 3.0% by mass, with respect to the total content of the compound represented by Formula (1) and the (meth)acrylate compound (2).

However, in a case in which the monomer composition for a dental material according to the present disclosure is used as a bonding material, or a pretreatment material such as a primer, the content of the compound represented by Formula (1) is preferably from 1.0% by mass to 95% by mass, and more preferably from 3.0% by mass to 60% by mass, with respect to the total content of the compound represented by Formula (1) and the (meth)acrylate compound (2).

[Method of Producing Compound Represented by Formula (1)]

The compound represented by Formula (1) is preferably obtained by the reaction of a compound (X) to be described later with a compound (Y) to be described later. More specifically, the compound represented by Formula (1) is preferably obtained by the reaction of at least one group selected from the group consisting of a hydroxy group, a primary amino group and a secondary amino group in the compound (X), with an isocyanate group in the compound (Y).

The compound (X), which is a raw material of the compound represented by Formula (1), may be, for example, a compound containing at least one selected from the group consisting of a hydroxy group, a primary amino group and a secondary amino group. Specifically, the compound (X) is a compound which has from 1 to 200 carbon atoms and contains at least one selected from the group consisting of an oxygen atom and a nitrogen atom, and in which the at least one selected from the group consisting of an oxygen atom and a nitrogen atom is bound to a hydrogen atom.

The compound (X) is preferably a compound in which at least one of the bonding positions "*" in any one of the above described Formulae (X1) to (X10) is bound to a hydrogen atom. Further, each bonding position "*" in any one of Formulae (X1) to (X10) may be bound to a hydrocarbon group, a (meth)acryloyl group or the like.

The compound (X) is preferably a compound in which two or more bonding positions "*" in any one of Formulae (X1) to (X10) are bound to hydrogen atoms, and more preferably bound to three hydrogen atoms.

The compound (Y), which is a raw material of the compound represented by Formula (1), may be, for example, a compound which contains an isocyanate group and a (meth)acryloyloxy group, and in which the isocyanate group and the (meth)acryloyloxy group are bound via a divalent organic group having from 2 to 6 carbon atoms.

Examples of the compound (Y) include a compound represented by the following Formula:

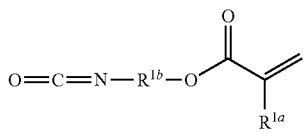

In the above Formula, $R^{1a}$ and $R^{1b}$ are the same as $R^{1a}$ and $R^{1b}$ in Formula (A) described above.

The reaction of the compound (X) with the compound (Y) may be carried out in the absence of a solvent, or in a solvent. Any known solvent which is inert in the reaction can be used as the solvent. Examples of the solvent include polar solvents, for example, hydrocarbon-based solvents such as n-hexane, benzene, toluene and xylene.

A catalyst may be added when the compound (X) is reacted with the compound (Y), from the viewpoint of improving reaction velocity. As the catalyst, it is possible to use a known catalyst that accelerates the reaction of at least one group selected from the group consisting of a hydroxy group, a primary amino group and a secondary amino group in the compound (X), with an isocyanate group in the compound (Y).

Examples of the catalyst include organic tin compounds such as dibutyltin dilaurate.

The amount of the catalyst to be used may be from 0.001% by mass to 0.1% by mass, or may be from 0.01% by mass to 0.1% by mass, with respect to the total amount of the compound (X) and the compound (Y).

The reaction is usually carried out at a reaction temperature within a range of from 20° C. to 120° C., and preferably from 30° C. to 100° C., but not particularly limited thereto.

The reaction is usually carried out for a reaction time of several minutes to several tens of hours, but not particularly limited thereto, because it varies depending on conditions such as reaction temperature. The end-point of the reaction can be confirmed by a method such as HPLC (high-speed liquid chromatography) analysis.

The compound (X) and the compound (Y) are preferably charged in amounts at a molar ratio (X:Y) of from 1:1 to 1:12, and more preferably from 1:1 to 1:6.

[Composition for Dental Material]

A composition for a dental material according to the present disclosure contains the monomer composition for a dental material according to the present disclosure, and a polymerization initiator. This composition for a dental material is chemically polymerizable, thermal polymerizable or photopolymerizable, and can be preferably used, for example, as a dental restorative material.

The content of the compound represented by Formula (1) in the composition for a dental material is preferably from 0.1% by mass to 20% by mass, more preferably from 0.5% by mass to 10% by mass, and still more preferably from 1.0% by mass to 8.0% by mass, with respect to the total mass of the composition for a dental material.

However, in the case of using as a bonding material or the like, the content of the compound represented by Formula (1) is preferably from 1.0% by mass to 80% by mass, more preferably from 3.0% by mass to 60% by mass, and still more preferably from 5.0% by mass to 40% by mass, with respect to the total mass of the composition for a dental material.

As the polymerization initiator, a polymerization initiator commonly used in the dental field can be used. The polymerization initiator is usually selected taking into consideration the polymerizability and polymerization conditions of a polymerizable compound, such as the compound represented by Formula (1), contained in the composition for a dental material.

In the case of performing chemical polymerization, the polymerization initiator is preferably, for example, a redox polymerization initiator, which is a combination of an oxidizing agent and a reducing agent. In the case of using a redox polymerization initiator, the oxidizing agent and the reducing agent, which are separately packaged, may be mixed immediately before use. The polymerization initiator is not particularly limited, and any known and commonly used polymerization initiator can be used, for example. The polymerization initiator is usually selected taking into consideration the polymerizability and polymerization conditions of the polymerizable compound.

For example, it is possible to use, as the polymerization initiator, a Redox polymerization initiator, such as: an organic peroxide (such as benzoyl peroxide, decanoyl peroxide or diacyl peroxide)-aromatic amine Redox system; a cumene hydroperoxide-thiourea Redox system; an ascorbic acid-copper salt Redox system; or an organic peroxide-amine compound-sulfinic acid (or a salt thereof) Redox system. Further, a catalyst based on a trialkylborane or a partial oxide thereof, such as tributylborane or partial oxide thereof, 5-butylbarbituric acid, 5-butyl-2-thiobarbituric acid or the like, is also suitably used, as the polymerization initiator.

In the case of performing thermal polymerization by heating, a polymerization initiator such as a peroxide or an azo-based compound is preferred.

The peroxide is not particularly limited, and examples thereof include benzoyl peroxide, t-butyl hydroperoxide and cumene hydroperoxide. The azo-based compound is not particularly limited, and examples thereof include azobisisobutyronitrile.

In the case of performing photopolymerization by visible light irradiation, examples of a photopolymerization catalyst to be used include: α-diketones such as camphorquinone and acetyl benzoyl; benzoyl alkyl ethers such as benzoyl ethyl ether; thioxanthone derivatives such as 2-chlorothioxanthone and methylthioxanthone; benzophenone derivatives such as benzophenone and p,p'-methoxybenzophenone; and acylphosphine oxides such as 2,4,6-trimethylbenzoyldiphenylphosphine oxide and 2,6-dimethoxybenzoyldiphenylphosphine oxide. Further, in addition to any of these polymerization initiators, it is preferred to use a co-catalyst component in combination. Examples of the co-catalyst component include: amine compounds such as dimethylaminoethyl methacrylate, N,N-dimethyl-p-toluidine and N,N-dimethylethyl benzoate; aldehyde compounds such as citronellal and dimethylaminobenzaldehyde; and thiol group-containing compounds such as 2-mercaptobenzoxazole and decanethiol.

The above described polymerization initiators may be used singly, or in combination of two or more kinds thereof. The amount of the polymerization initiator to be incorporated is preferably from 0.01% by mass to 20% by mass, and more preferably from 0.1% by mass to 5% by mass, with respect to 100% by mass of the composition for a dental material.

The composition for a dental material according to the present disclosure may contain a filler. The filler to be used is not particularly limited, and any filler commonly used in the dental field can be used. Fillers are usually classified into organic fillers and inorganic fillers.

Examples of organic fillers include fine powders of polymethyl methacrylate, methyl methacrylate-ethyl methacrylate copolymers, ethylene-vinyl acetate copolymers, and styrene-butadiene copolymers.

Examples of inorganic fillers include fine powders of: various types of glasses (which contain a silicon dioxide as a main component, and, if necessary, an oxide of a heavy metal, boron, aluminum or the like), various types of ceramics, diatomaceous earth, kaolin, clay minerals (such as montmorillonite), activated white clay, synthetic zeolite, mica, calcium fluoride, ytterbium fluoride, calcium phosphate, barium sulfate, zirconium dioxide, titanium dioxide, and hydroxyapatite.

Specific examples of such inorganic fillers include barium borosilicate glasses (such as Schott 8235, Schott GM27884 and Schott G018-053), strontium boroaluminosilicate glasses (such as Schott G018-163), lanthanum glasses (such as Schott GM31684), fluoroaluminosilicate glasses (such as Schott G018-117), and boroaluminosilicate glasses containing zirconium, cesium etc. (such as Schott G018-307).

Further, it is also possible to use an organic-inorganic composite filler, which is obtained by adding a polymerizable compound to an inorganic filler in advance, forming the mixture into a paste, and then curing the resultant by polymerization, followed by crushing.

The composition for a dental material into which a microfiller having a particle size of 0.1 μm or less is incorporated, is one embodiment of the composition for a dental material suitable for a dental composite resin. Such a filler having a small particle size is preferably made of a material such as silica (for example, AEROSIL (brand name)), alumina, zirconia or titania. Incorporation of such an inorganic filler having a small particle size is advantageous in obtaining polishing lubricity of a cured product of a composite resin.

These fillers may be surface treated by a surface treatment agent such as a silane coupling agent, depending on the purpose. Examples of the surface treatment agent to be used include known silane coupling agents, for example, organosilicon compounds such as methacryloxyalkyltrimethoxysilanes (the number of carbon atoms between the methacryloxy group and the silicon atom: 3 to 12), methacryloxyalkyltriethoxysilanes (the number of carbon atoms between the methacryloxy group and the silicon atom: 3 to 12), vinyltrimethoxysilane, vinylethoxysilane and vinyltriacetoxysilane.

These fillers may be used singly, or in combination of two or more kinds thereof. The amount of the filler to be incorporated may be selected as appropriate, taking into consideration the handleability (viscosity) of the composition for a dental material (such as a composite resin composition), the flexural strength of a cured product thereof, and the like. The amount of the filler to be incorporated is preferably from 10 parts by mass to 2,000 parts by mass, more preferably from 50 parts by mass to 1,000 parts by mass, and still more preferably from 100 parts by mass to 600 parts by mass, with respect to 100 parts by mass of all components other than the filler contained in the composition for a dental material.

If appropriate, the composition for a dental material according to the present disclosure may contain a component other than the monomer composition according to the present disclosure and the polymerization initiator, depending on the purpose. The component which may be contained in the composition for a dental material according to the present disclosure is not particularly limited, as long as the component is a known one. For example, the composition may contain a polymerization inhibitor, for the purpose of improving the storage stability. Further, the composition may contain a pigment, such as a known pigment or dye, for the purpose of adjusting color. In addition, the composition may contain a reinforcing material, such as known fibers, for the purpose of improving the strength of the resulting cured product. If necessary, the composition for a dental material according to the present disclosure may contain a solvent (such as acetone or distilled water) and/or an additive(s)

such as a bactericide, a disinfectant, a stabilizer and/or a preservative, as long as the effects of the present disclosure can be achieved.

The composition for a dental material according to the present disclosure can be cured, by any of the polymerization methods using the polymerization initiators described above, under appropriate conditions. For example, in the case of the composition for a dental material according to the present disclosure, which contains a photopolymerization initiator which initiates polymerization by visible light irradiation, a desired cured product can be obtained by processing the composition for a dental material into a predetermined shape, and irradiating visible light for a predetermined period of time, using a known light irradiation apparatus. Conditions such as irradiation intensity and irradiation intensity can be changed as appropriate, depending on the curability of the composition for a dental material. The resulting cured product which has been cured by irradiating light, such as visible light, may further be subjected to a heat treatment under appropriate conditions, to improve the flexural strength of the cured product.

[Dental Material]

A dental material according to the present disclosure is a cured product of the composition for a dental material according to the present disclosure. Curing conditions for the composition for a dental material may be selected as appropriate, depending on the composition of the composition for a dental material, the application of the resulting dental material and the like.

The thus obtained cured product of the composition for a dental material according to the present disclosure can be suitably used as a dental material.

The method of using the composition for a dental material according to the present disclosure is not particularly limited, as long as the method is commonly known as a method of using a dental material. For example, in the case of using the composition for a dental material according to the present disclosure as a composite resin for filling a caries cavity, this objective can be achieved by filling the composition for a dental material into a caries cavity in the oral cavity, and then photocuring the composition using a known light irradiation apparatus. In the case of using the composition for a dental material as a composite resin for a tooth crown, a desired tooth crown material can be obtained by processing the composition for a dental material into an appropriate shape, photocuring the composition using a known light irradiation apparatus, and further performing a heat treatment under predetermined conditions.

The composition for a dental material or the dental material according to the present disclosure can be preferably used, for example, as a denture base resin, a denture base lining material, an impression material, a cementing material (such as a resin-added glass ionomer cement), a dental adhesive (such as a dental adhesive resin cement, a tooth-fissure sealant, a dental bonding material or an orthodontic adhesive), a resin block for CAD/CAM (for forming an inlay, an onlay, a crown, a temporary crown or the like), a dental restorative filling material (such as a dental composite resin, or a composite resin for abutment construction), a hard resin, an artificial tooth material or the like. Among these, the composition for a dental material or the dental material according to the present disclosure is particularly suitable for a dental composite resin, a dental adhesive resin cement, a dental bonding material or the like.

EXAMPLES

Examples of the present disclosure will now be described, but the present disclosure is in no way limited by the following Examples. Abbreviations of compounds used in the Examples of the present disclosure are shown below.

[Polyfunctional Glycerol (Meth)acrylate Compounds (A)]

TMOIG: trimethacryloyloxyethyl carbonyl aminoglycerol: a compound represented by the following Formula (1-1) (a compound synthesized by allowing methacryloyloxyethyl isocyanate (MOI, manufactured by Showa Denko K.K.) to react with glycerol (manufactured by Sigma-Aldrich Inc.) at a molar ratio of 1:3, in accordance with a known urethanization reaction method)

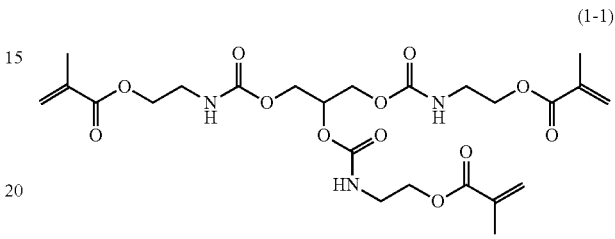

(1-1)

DMOIG: dimethacryloyloxyethyl carbonyl aminoglycerol: a mixture of a compound represented by the following Formula (1-2) and a compound represented by the following Formula (1-3) (a mixture of compounds each synthesized by allowing methacryloyloxyethyl isocyanate (MOI, manufactured by Showa Denko K.K.) to react with glycerol (manufactured by Sigma-Aldrich Inc.) at a molar ratio of 1:2, in accordance with a known urethanization reaction method)

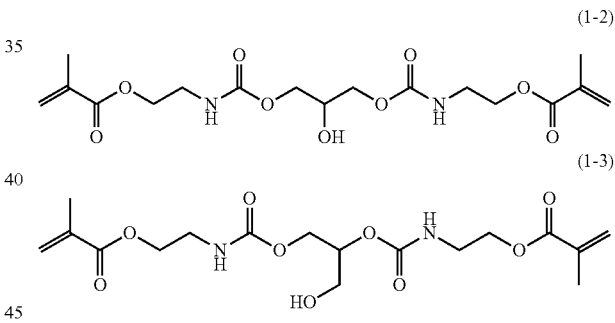

[Polymerizable Monomers (B)]

UDMA: 2,2,4-trimethylhexamethylene bis(2-carbamoyloxyethyl) dimethacrylate (a compound synthesized by allowing 2,2,4-trimethylhexyl diisocyanate (TMHDI, manufactured by Tokyo Chemical Industry Co., Ltd.) to react with 2-hydroxyethyl methacrylate (HEMA, manufactured by Mitsubishi Chemical Corporation) at a molar ratio of 1:2, in accordance with a known urethanization reaction method)

TEGDMA: triethylene glycol dimethacrylate (manufactured by Shin-Nakamura Chemical Co., Ltd.)

HEMA: 2-hydroxyethyl methacrylate (manufactured by Mitsubishi Chemical Corporation)

[Acidic Group-containing Polymerizable Monomers (C)]

4-MET: 4-methacryloyloxyethyl trimellitic acid (a compound synthesized by allowing 4-methacryloyloxyethyl trimellitic anhydride (manufactured by FUJIFILM Wako Pure Chemical Corporation) to react with 1.2 equivalent of distilled water)

MDP: 10-methacryloyloxydecyl dihydrogen phosphate (manufactured by FUJIFILM Wako Pure Chemical Corporation)

[Fillers (D)]
R812: silica microparticles (brand name: AEROSIL R812, manufactured by Nippon Aerosil Co., Ltd.)
8235: silane-treated barium glass powder (brand name: "8235"; particle size: 0.7 m; treated with γ-MPTS at 6% with respect to the mass of the filler; manufactured by SCHOTT AG)
GM27884: silane-treated barium glass powder (brand name: "GM27884"; particle size: 1.5 m; treated with γ-MPTS at 1.6% with respect to the mass of the filler; manufactured by SCHOTT AG)
[Solvents (E)]
Acetone: manufactured by FUJIFILM Wako Pure Chemical Corporation)
Distilled water: one produced by an apparatus for producing distilled water (manufactured by Tokyo Rikakikai Co., Ltd.)
[Photopolymerization Initiators (F)]
CQ: d,l-camphorquinone (manufactured by FUJIFILM Wako Pure Chemical Corporation)
DMABAE: N,N-dimethylethyl benzoate (manufactured by FUJIFILM Wako Pure Chemical Corporation)
[Other Components: Polymerization Inhibitors]
BHT: 2,6-di-t-butyl-4-methylphenol (manufactured by Tokyo Chemical Industry Co., Ltd.)
MEHQ: 4-methoxyphenol (manufactured by FUJIFILM Wako Pure Chemical Corporation)

Examples 1 to 8 and Comparative Examples 1 to 4

<Preparation of Compositions for Dental Materials>
Respective components are mixed in the amounts shown in Table 1 to be described later, to prepare compositions for dental materials to be used as dental composite resins of Example 1, Example 2, Example 3 and Comparative Example 1. Respective components are mixed in the amounts shown in Table 2 to be described later, to prepare compositions for dental materials to be used as dental bonding materials of Example 4, Example 5 and Comparative Example 2. Respective components are mixed in the amounts shown in Table 3 and Table 4 to be described later, to prepare compositions for dental materials to be used as dental self-adhesive resin cements of Example 6, Example 7, Example 8, Comparative Example 3 and Comparative Example 4.
<Method of Measuring Three-point Flexural Strength of Dental Compositions: Examples 1 to 3 and 6 to 8, and Comparative Examples 1, 3 and 4>
At room temperature controlled to from 20 to 25° C., each of the compositions for dental materials of Example 1, Example 2, Example 3, Example 6, Example 7, Example 8, Comparative Example 1, Comparative Example 3 and Comparative Example 4 which had been collected on a dental paper for kneading, was filled into a mold for preparing a test body having a size of 2 mm×2 mm×25 mm, and Lumiler films were pressed thereagainst from both top and bottom surfaces. Each mold filled with each composition for a dental material was set to an LED (light emitting diode) irradiation apparatus for working (ALPHA LIGHT V, manufactured by Morita Corporation), and light irradiation was carried out three minutes per each of the top and bottom surfaces, and the resulting cured body was used as a test body.
Each test body was removed from the mold, immersed in distilled water, and stored in an incubator controlled to 37±1° C. for 18 hours. Thereafter, the test body was taken out of the incubator, and a three-point flexural test was carried out using a compact desktop tester (manufactured by Shimadzu Corporation). The test was performed by applying a load until the test body breaks, at a rate of loading of a crosshead speed of 1 mm/min, and the strength of each cured body was calculated from the thus obtained maximum point stress. The elastic modulus of the cured body was also calculated at this time. The results thereof are shown in Table 1 described below.

TABLE 1

|  | Example 1 | Example 2 | Example 3 | Comparative Example 1 |
|---|---|---|---|---|
| UDMA | 70 | 65 | 70 | 70 |
| TEGDMA | 25 | 30 | 10 | 30 |
| TMOIG | 5 | 5 | 20 | — |
| CQ | 0.3 | 0.3 | 0.3 | 0.3 |
| DMDBAE | 0.6 | 0.6 | 0.6 | 0.6 |
| BHT | 0.2 | 0.2 | 0.2 | 0.2 |
| MEHQ | 0.1 | 0.1 | 0.1 | 0.1 |
| R812 | 10 | 10 | 10 | 10 |
| 8235 | 70 | 70 | 70 | 70 |
| GM27884 | 150 | 150 | 150 | 150 |
| Mechanical properties | | | | |
| Three-point flexural strength | 141.3 MPa | 137.3 MPa | 146.0 MPa | 135.9 MPa |
| SD | 4.3 | 10.9 | 1.4 | 8.2 |
| Elastic modulus | 7.2 GPa | 7.8 GPa | 8.1 GPa | 7.0 GPa |
| SD | 0.2 | 0.6 | 0.2 | 0.2 |

As shown in Table 1, in applications as dental composite resins, the compositions for dental materials of Example 1, Example 2 and Example 3, which contain TMOIG, showed better mechanical properties (three-point flexural strength and elastic modulus) as compared to the dental composite resin composition of Comparative Example 1, which does not contain TMOIG The notation "-" in the Table indicates that the corresponding component is not contained. Further, the notation "SD" in the Table stands for standard deviation. The same applies to the descriptions in the following Tables.
<Method of Evaluating Adhesive Strength>
Bovine mandibular anterior teeth, which had been stored frozen after extraction, were thawed under pouring water, and subjected to root amputation and dental pulp extraction, to be used as bovine teeth as adherends. Each resulting bovine tooth was placed in a plastic cylindrical container having a diameter of 25 mm and a depth of 25 mm, and embedded in an acrylic resin. Each bovine tooth as an adherend was polished using a water-proof emery paper (Pa 400) to expose a smooth surface of enamel or dentin, immediately before use. The adhesive strength was determined by applying a shear load at a crosshead speed of 1.0 mm/min, in a direction parallel to the enamel or dentin surface of the bovine tooth and so as to be in contact with the surface, and measuring the shear load at which a cured product which had been formed in the form of a column on the surface of the bovine tooth was separated from the tooth surface.
The method of processing each composition for a dental material is shown below.
<Method of Evaluating Adhesive Strength of Dental Bonding Materials: Examples 4 and 5, and Comparative Example 2>
Each of the compositions for dental materials of Example 4, Example 5 and Comparative Example 2 was coated on the flat surface of the enamel or dentin of each bovine tooth, after drying the surface to be adhered of the tooth by spraying compressed air for about one second. Twenty seconds later, a volatile solvent contained in each composition for a dental material was dried by a dental air syringe. Thereafter, each composition for a dental material was irradiated with light for 20 seconds, using an LED visible light irradiation apparatus (TRANSLUX 2WAVE) to cure the composition. Then a plastic mold (manufactured by Ultradent Products, Inc.) having a diameter of 2.38 mm was set on the coated tooth surface, filled with a photopolymerizable material (CLEARFIL EPX, manufactured by Kuraray Noritake Dental Inc.), and irradiated with light for 20 seconds, using the same LED visible light irradiation apparatus. Thereafter, the resultant was immersed in water, stored in an incubator controlled to 37° C. for 18 hours, and then the adhesive strength was measured. The results thereof are shown in Table 2 described below.

TABLE 2

|  | Example 4 | Example 5 | Comparative Example 2 |
| --- | --- | --- | --- |
| UDMA | 25 | 10 | 25 |
| HEMA | 5 | 5 | 5 |
| TMOIG | 5 | 25 | — |
| MDP | 10 | 10 | 10 |
| BHT | 0.1 | 0.1 | 0.1 |
| CQ | 0.6 | 0.6 | 0.6 |
| DMABAE | 0.6 | 0.6 | 0.6 |
| Acetone | 40 | 40 | 45 |
| H20 | 15 | 15 | 15 |
| Adhesion to tooth substances | | | |
| Enamel | 23.7 MPa | 24.6 MPa | 22.5 MPa |
| SD | 2.0 | 2.6 | 0.9 |
| Dentin | 10.7 MPa | 10.9 MPa | 9.5 MPa |
| SD | 0.6 | 2.4 | 0.8 |

As shown in Table 2, in applications as dental boding materials, the compositions for dental materials of Example 4 and Example 5, which contain TMOIG, showed a better adhesion to tooth substances as compared to the composition of Comparative Example 2, which does not contain TMOIG <Method of Evaluating Adhesive Strength of Dental Self-adhesive Resin Cements: Examples 6 to 8, and Comparative Examples 3 and 4>

The surface to be adhered of the enamel or dentin of each bovine tooth was dried by spraying compressed air for about one second. Subsequently, each of the compositions for dental materials of Examples 6 to 8 as well as Comparative Examples 3 and 4 was coated on the surface to be adhered of a cylindrical column-shaped cured product (diameter: 2.3 mm×height: 2.2 mm) of a photocurable composition (CLEARFIL EPX, manufactured by Kuraray Noritake Dental Inc.) which had been separately prepared in advance. The cured product was then set on the surface to be adhered of the bovine tooth, and pressed thereagainst using a dedicated jig, at a force of 5 N. Thereafter, an excessive amount of each composition for a dental material was removed, and the composition was irradiated with light using an LED visible light irradiation apparatus (TRANSLUX 2WAVE, manufactured by Kulzer Japan Co., Ltd.) from four directions, for 10 seconds in each direction, to cure the composition. Thereafter, the resultant was immersed in water, stored in an incubator controlled to 37° C. for 18 hours, and then the adhesive strength was measured. Examples in which MDP and 4-MET were used as the acidic group-containing polymerizable monomers (C) (Examples 6 and 7, and Comparative Example 3) are shown in Table 3; and examples in which MDP alone was used as the acidic group-containing polymerizable monomer (C) (Example 8 and Comparative Example 4) are shown in Table 4.

TABLE 3

|  | Example 6 | Example 7 | Comparative Example 3 |
| --- | --- | --- | --- |
| UDMA | 55 | 55 | 60 |
| TEGDMA | 30 | 30 | 30 |
| TMOIG | 5 | — | — |
| DMOIG | — | 5 | — |
| MDP | 5 | 5 | 5 |
| 4MET | 5 | 5 | 5 |
| CQ | 0.5 | 0.5 | 0.5 |
| DMABAE | 1.0 | 1.0 | 1.0 |
| GM27884 | 150 | 150 | 150 |
| Adhesion to tooth substances | | | |
| Enamel | 27.6 MPa | — | 25.5 MPa |
| SD | 4.8 | — | 1.0 |
| Dentin | 19.4 MPa | 19.9 MPa | 16.0 MPa |
| SD | 3.6 | 2.4 | 3.8 |
| Mechanical properties | | | |
| Three-point flexural strength | 147 MPa | 130 MPa | 127 MPa |
| SD | 12.0 | 7.0 | 9.0 |

TABLE 4

|  | Example 8 | Comparative Example 4 |
| --- | --- | --- |
| UDMA | 55 | 65 |
| TEGDMA | 30 | 30 |
| TMOIG | 10 | — |
| MDP | 5 | 5 |
| CQ | 0.5 | 0.5 |
| DMABAE | 1.0 | 1.0 |
| GM27884 | 150 | 150 |
| Adhesion to tooth substances | | |
| Enamel | 23.5 MPa | 19.2 MPa |
| SD | 1.5 | 2.5 |
| Dentin | 25.1 MPa | 18.7 MPa |
| SD | 3.4 | 1.5 |
| Mechanical properties | | |
| Three-point flexural strength | 140 MPa | 131 MPa |
| SD | 8.9 | 9.7 |

As shown in Table 3 and Table 4, in applications as dental self-adhesive resin cements, the compositions for dental materials of Examples 6 to 8, which contain TMOIG or DMOIG, showed a better flexural strength as compared to the composition of Comparative Example 3 or Comparative Example 4, which does not contain TMOIG and DMOIG Further, the compositions for dental materials of Examples 6 to 8 showed a better adhesion to tooth substances as compared to the composition of Comparative Example 3 or Comparative Example 4. In particular, it has been found out that the compositions for dental materials of Examples 6 and 8, which contain TMOIG, show an excellent flexural strength.

It has been found out from the above results that the incorporation of TMOIG or DMOIG into a composition for a dental material imparts an excellent flexural strength to the cured product thereof. Further, it has been found out that the incorporation of TMOIG or DMOIG into a composition for a dental material enables to obtain a favorable adhesion to tooth substances.

The disclosure of Japanese Patent Application No. 2018-247972, filed on Dec. 28, 2018, is incorporated herein by reference in their entirety.

All publications, patent applications, and technical standards mentioned in the present specification are incorporated herein by reference to the same extent as if such individual publication, patent application, or technical standard was specifically and individually indicated to be incorporated by reference.

The invention claimed is:

1. A composition for a dental material, comprising:
a monomer composition; and
a polymerization initiator,
the monomer composition comprising a compound represented by the following Formula (1):

$$X\!-\!(Y)_n \quad (1)$$

wherein, in Formula (1):

X represents an n-valent organic group having from 1 to 200 carbon atoms and containing at least one selected from the group consisting of an oxygen atom and a nitrogen atom, wherein the at least one selected from the group consisting of an oxygen atom and a nitrogen atom is bound to Y;

each Y represents a (meth)acryloyl group-containing group (Y1) represented by the following Formula (A), a (meth)acryloyl group (Y2), a hydrogen atom, or a hydrocarbon group having from 1 to 20 carbon atoms, with the proviso that at least one or more Y, among all Ys included in the compound represented by Formula (1), is the (meth)acryloyl group-containing group (Y1);

a plurality of Ys may be the same as or different from each other; and n represents an integer of 3 or more $$\left( \begin{array}{c} O \\ \parallel \\ C \\ | \\ N-R^{1b}-O \\ | \\ H \end{array} \begin{array}{c} O \\ \parallel \\ C \\ | \\ R^{1a} \end{array} \right) \quad (A)$$

wherein, in Formula (A), $R^{1a}$ represents a hydrogen atom or a methyl group; and $R^{1b}$ represents a divalent organic group having from 2 to 6 carbon atoms, which may be substituted with an alkyl group having from 1 to 6 carbon atoms or a (meth)acryloyloxyalkylene group, wherein X is any one of groups represented by the following Formulae (X1) to (X10):

$$*\!-\!O\!-\!CH_2\!-\!\underset{\underset{*}{|}}{\overset{\overset{*}{|}}{C}H}\!-\!CH_2\!-\!O\!-\!* \quad (X1)$$

$$*\!-\!O\!-\!CH_2\!-\!\underset{\underset{CH_2CH_3}{|}}{\overset{\overset{*}{|}\;O\;|\;CH_2\;|}{C}}\!-\!CH_2\!-\!O\!-\!* \quad (X2)$$

$$*\!-\!O\!-\!CH_2\!-\!\underset{\underset{\underset{*}{|}\;O\;|\;CH_2\;|}{CH_2\;|}}{\overset{\overset{*}{|}\;O\;|\;CH_2\;|}{C}}\!-\!CH_2\!-\!O\!-\!* \quad (X3)$$

(X4) — a chain $*\!-\!O\!-\!C\!-\!C\!-\!C\!-\!C\!-\!C\!-\!C\!-\!O\!-\!*$ with H, O*, H, O*, O*, H above and H, H, O*, H, H, H below $$(X5)\; *\!-\!O\!-\!CH_2\!-\!C(CH_2O^*)(CH_2O^*)\!-\!CH_2\!-\!O\!-\!CH_2\!-\!C(CH_2O^*)(CH_2O^*)\!-\!CH_2\!-\!O\!-\!*$$

(X6) $*\!-\!O\!-\!CH_2\!\cdot\!C(CH_2O^*)(CH_2O^*)\!-\!CH_2\!\cdot\!O\!-\!CH_2\!\cdot\!C(CH_2O^*)(CH_2O^*)\!-\!CH_2\!\cdot\!O\!-\!CH_2\!\cdot\!C(CH_2O^*)(CH_2O^*)\!-\!CH_2\!\cdot\!O\!-\!*$ (X7) $*\!-\!O\!-\!(CH_2\!-\!CH(O^*)\!-\!CH_2\!-\!O)_{n^7}\!-\!CH_2\!-\!CH(O^*)\!-\!CH_2\!-\!O\!-\!*$ (X8) $*\!-\!O\!-\!CH_2CH_2\!-\!N(CH_2CH_2O^*)\!-\!CH_2CH_2\!-\!O\!-\!*$

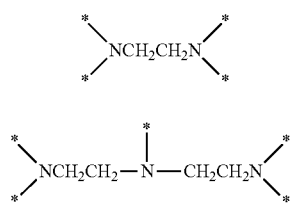

(X9)

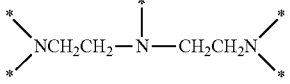

(X10)

wherein, in Formulae (X1) to (X10), each * represents a bonding position; and wherein, in Formula (X7), $n^{X7}$ represents an integer from 1 to 40.

2. The composition for a dental material according to claim 1, wherein the compound represented by Formula (1) has a molecular weight of from 350 to 2,000.

3. The composition for a dental material according to claim 1, wherein at least two or more Ys, among all the Ys included in the compound represented by Formula (1), are the (meth)acryloyl group-containing group (Y1).

4. The composition for a dental material according to claim 1, wherein, in Formula (A), $R^{1b}$ is a linear alkylene group having from 2 to 6 carbon atoms or a linear oxyalkylene group having from 2 to 6 carbon atoms.

5. The composition for a dental material according to claim 1, wherein n is an integer from 3 to 12.

6. The composition for a dental material according to claim 1, wherein, in Formula (1), the at least one (meth)acryloyl group-containing group (Y1) comprises at least one selected from the group consisting of groups represented by the following Formulae (Y1a) to (Y1f):

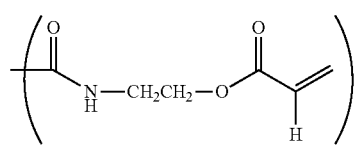

(Y1a)

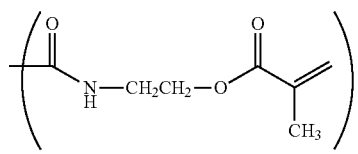

(Y1b)

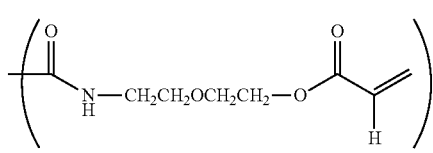

(Y1c)

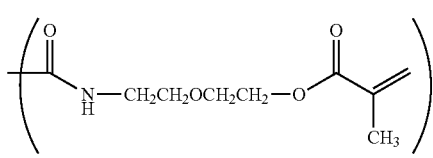

(Y1d)

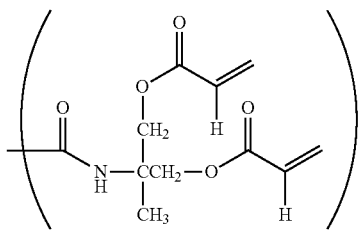

(Y1e)

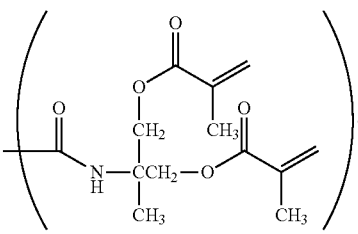

(Y1f)

7. The composition for a dental material according to claim 1, the monomer composition comprising, as the compound represented by Formula (1), at least one selected from the group consisting of the following compounds (1-1) to (1-10):

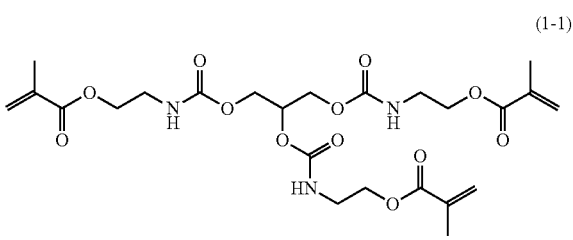

(1-1)

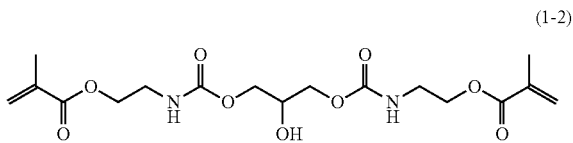

(1-2)

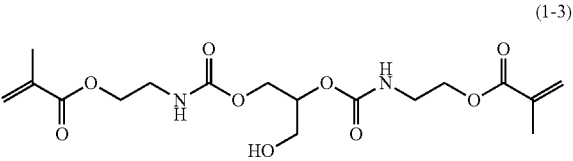

(1-3)

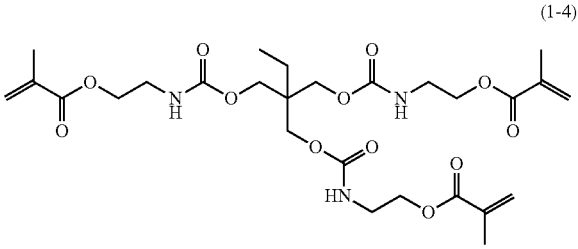

(1-4)

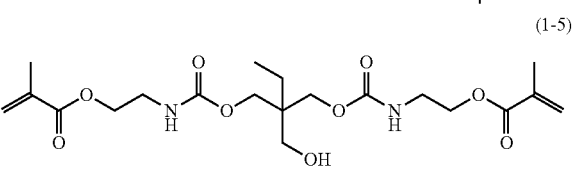

(1-5)

-continued

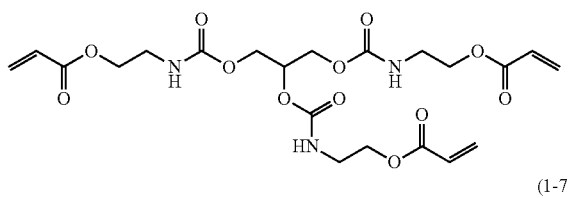

(1-6)

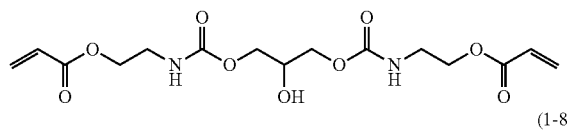

(1-7)

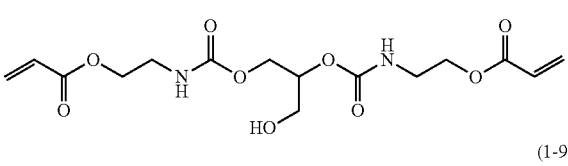

(1-8)

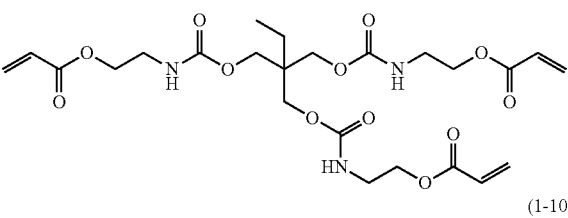

(1-9)

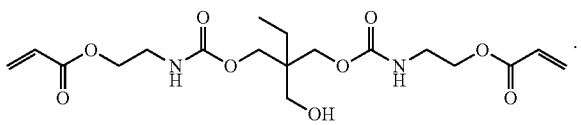

(1-10)

8. The monomer composition for a dental material according to claim 1, the monomer composition further comprising a (meth)acrylate compound (2) other than the compound represented by Formula (1).

9. The composition for a dental material according to claim 8, wherein a content of the compound represented by Formula (1) is from 1.0% by mass to 40.0% by mass, with respect to a total content of the compound represented by Formula (1) and the (meth)acrylate compound (2).

10. The composition for a dental material according to claim 8, wherein the (meth)acrylate compound (2) is one or more compounds selected from the group consisting of an acidic group-containing (meth)acrylate, a monofunctional (meth)acrylate containing no acidic group, and a bifunctional (meth)acrylate containing no acidic group.

11. The composition for a dental material according to claim 8, wherein a total content of the compound represented by Formula (1) and the (meth)acrylate compound (2) is 90% by mass or more, with respect to a total amount of the composition for a dental material.

12. The composition for a dental material according to claim 1, wherein a content of the compound represented by Formula (1) is from 0.1% by mass to 20% by mass, with respect to a total mass of the composition for a dental material.

13. The composition for a dental material according to claim 1, wherein the composition is used as a dental adhesive resin cement, a dental composite resin, or a dental bonding material.

14. A dental material which is a cured product of the composition for a dental material according to claim 1.

15. A dental treatment method, comprising curing the composition for a dental material according to claim 1 in an oral cavity.

* * * * *